US008946288B1

(12) United States Patent
Pan et al.

(10) Patent No.: US 8,946,288 B1
(45) Date of Patent: Feb. 3, 2015

(54) USES OF HYDROXYL POLYMETHOXYLFLAVONES (HPMFS) AND DERIVATIVES THEREOF

(71) Applicants: Greenyn Biotechnology Co., Ltd, Taichung (TW); Min-Hsiung Pan, Kaohsiung (TW)

(72) Inventors: Min-Hsiung Pan, Kaohsiung (TW); Chia-Li Wu, Taichung (TW)

(73) Assignees: Min-Hsiung Pan, Kaohsiung (TW); Greenyn Biotechnology Co., Ltd., Taichung (TW)

(*) Notice: Subject to any disclaimer, the term of this patent is extended or adjusted under 35 U.S.C. 154(b) by 0 days.

(21) Appl. No.: 14/165,860

(22) Filed: Jan. 28, 2014

(30) Foreign Application Priority Data

Aug. 16, 2013 (TW) ............................ 102129499 A

(51) Int. Cl.

| | |
|---|---|
| ***A61K 31/352*** | (2006.01) |
| ***C07D 311/30*** | (2006.01) |
| ***A61K 31/353*** | (2006.01) |
| ***A61K 36/752*** | (2006.01) |

(52) U.S. Cl.
CPC ............ *A61K 31/353* (2013.01); *A61K 36/752* (2013.01)
USPC ........................... 514/456; 549/399; 549/403

(58) Field of Classification Search
USPC .................................. 514/456; 549/399, 403
See application file for complete search history.

(56) References Cited

FOREIGN PATENT DOCUMENTS

CN 200710051692.2 9/2008

OTHER PUBLICATIONS

Mei-Chun Kou et al., Effects of citrus flavonoids, 5-hydroxy-3,6,7,8,3',4'-hexamethoxyflavone and 3,5,6,7,8,3',4'heptamethoxyflavone, on the activities of macrophage scavenger receptors and the hepatic LDL receptor, 2013, Food Funct., 4, 602-609.*

Polymethoxyflavones Activate Ca2+-Dependent Apoptotic Targets in Adipocytes, Igor N. Sergeev, et al., Journal of Agricultural and Food Chemistry, 2009, 57, 5771-5776.

* cited by examiner

*Primary Examiner* — Kristin Vajda
(74) *Attorney, Agent, or Firm* — Ming Chow; Sinorica, LLC

(57) ABSTRACT

The invention discloses the uses of hydroxyl polymethoxylflavones and derivative thereof that are relative to inhibit adipogenesis and lower lipid accumulation, wherein the hydroxyl polymethoxylflavones is obtained from the peels of *Citrus* genus plants. Therefore, the hydroxyl polymethoxylflavones that of a therapeutically effective amount not only can be a medical compound for treatment obesity or fatty liver, but also can be a food element.

4 Claims, 16 Drawing Sheets

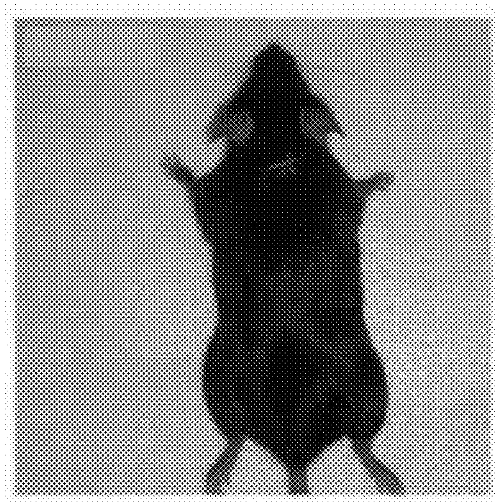
Fig. 10A
Fig. 10B
Fig. 10C
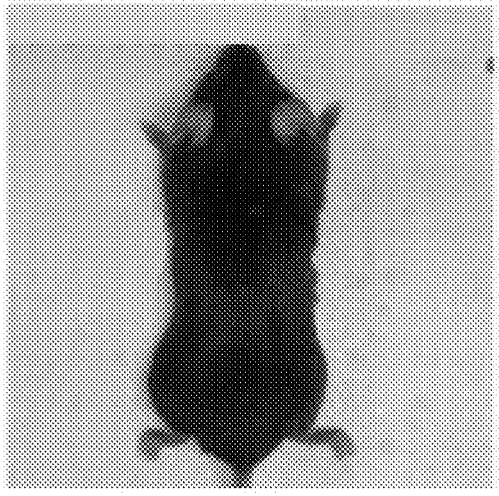
Fig. 10D

USES OF HYDROXYL POLYMETHOXYLFLAVONES (HPMFS) AND DERIVATIVES THEREOF

CROSS-REFERENCE TO RELATED APPLICATION

The current application claims a foreign priority to the patent application of Taiwan No. 102129499 filed on Aug. 16, 2013.

FIELD OF THE INVENTION

The present invention relates generally to the uses of the nature compound. In particular, the present invention relates to uses of hydroxyl polymethoxylflavones (HPMFs) and derivatives thereof.

BACKGROUND OF THE INVENTION

According to the previous reports, obesity is resulted from that assimilated calorie is much than consumption. The excessive calorie is stored as triglyceride (hereinafter referred to as TG) in adipose tissue and thereby accumulated in pancreas, liver, skeleton muscle. The accumulation of triglyceride in these indicated organs causes obesity and metabolic syndrome such as cardiovascular diseases, hypertension, hyperlipidemia and type II diabetes. Currently, WHO has been categorized obesity as a chronic illness disease. In Taiwan, the nutritional health reports from 2004 to 2008 had suggested that the excessive nutrition would cause the occurrence of many chronic illness diseases.

The obesity could be cured by various therapy approaches such as exercise, calorie control and surgery. However, eating out is the common dietary habit of people in the rush modem world. Therefore, the rush modem life style makes it difficult to low body weight through exercise and calorie control. Furthermore, the cost of the surgeries for lowing body weight such as cosmetic surgery and laparoscopic gastric bypass surgery are quite expansive. In addition to the expansive cost, the surgeries may bring some uncertain risk for the safety of patients. Some pharmaceutical approaches such as metabolic stimulus, appetite inhibitor and starch blocker are approached to low the body weight. However, intake of these drugs for a long term will bring some side effects to the subjects. In order to avoid the side effects of these available drugs, many investigations have suggested that the nature compounds and extracts are capable of lowing body weight through inhibiting appetite or accelerating the metabolism of energy. For example, caffeine accelerates energy metabolism through inhibition of phosphodiesterase activity to increase the cyclic adenosine monophosphate. The extract of *Hoodia* Cactus is capable of suppressing the appetite; the extract of *Prunella vulgaris* is able to be the starch blocker through inhibiting the enzyme activity of salivary amylase; the extract of *Semen plantaginis* is capable of lowing the concentration of TG in blood by accelerating the lipid metabolism.

Because these indicated natural extracts do not achieve the purpose for lowing weight through controlling the cell cycle of adipocytes, inhibiting adipocytes differentiation, promoting the lipolysis in adipocytes, the functions of these extracts are not efficient and obvious. Therefore, the current investigations have focused on development of new natural compounds for controlling behavior of adipocytes or suppressing the lipogenesis to efficiently suppress the lipid accumulation and obesity.

SUMMARY OF THE INVENTION

The present invention relates a hydroxyl polymethoxylflavones compound, hereinafter referred to as a HPMFs compound, which is extracted from citrus fruits. The HPMFs compound has ability for inhibition of lipogenesis and adipocyte differentiation, and decreasing the lipid accumulation surrounding the internal organs without alteration on the rate of food intake. Therefore, the HPMFs compound or derivative thereof can serve as an active ingredient of a composition for treating or preventing obesity-related diseases.

It is an object of the present invention provides a method of treating or preventing obesity-related diseases comprising administering to a subject a composition in a effective amount, wherein the composition including a HPMFs compound or a pharmaceutically acceptable salt thereof, or mixture thereof.

According to the present invention, the HPMFs compound is extracted from a peel of citrus fruit, wherein, the citrus fruit would be pomelo, mandarin orange, orange, kumquat or lemon.

In one embodiment of the present invention, the HPMFs compound is extracted by the following steps: (A) taking a predetermined amount extract from the peel of citrus fruit; (B) dissolving the extract with alcohols and adding hydrochloric acid to obtain a mixture; (C) incubating the mixture with heating circumfluence and then removing alcohols from the mixture; (D) extracting the mixture of the step C by water and an organic solvent; (E) collecting the organic solvent phase and purifying to obtain the HPMFs compound.

According to the present invention, the obesity-related disease is including, but not limiting to, obesity, fatty liver, metabolic syndrome, insulin resistance syndrome, cardiovascular disease, hypertension and hyperlipidemia.

BRIEF DESCRIPTION OF THE DRAWINGS

FIG. 10A~10D show the gross views of the each group mice with different administrations.

DETAILED DESCRIPTION OF THE INVENTION

Figure 1A:
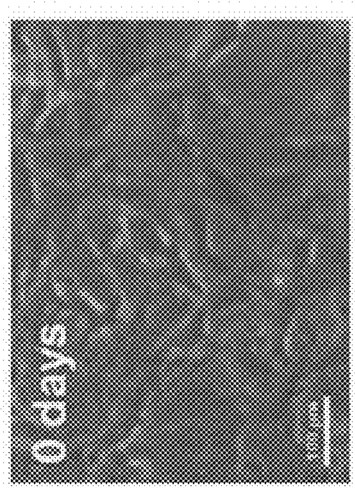
FIG. 1A shows the cellular morphology of cultured 3T3-L1 pre-adipocytes on day 0.
Figure 1B:
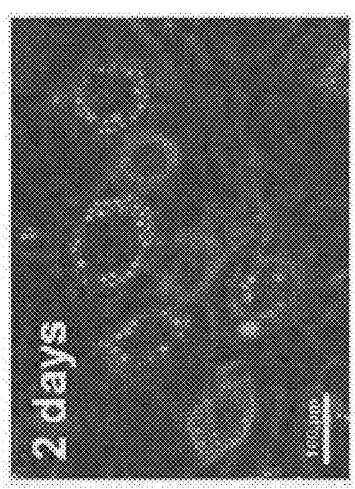
FIG. 1B shows the cellular morphology of cultured 3T3-L1 pre-adipocytes on day 2.
Figure 1C:
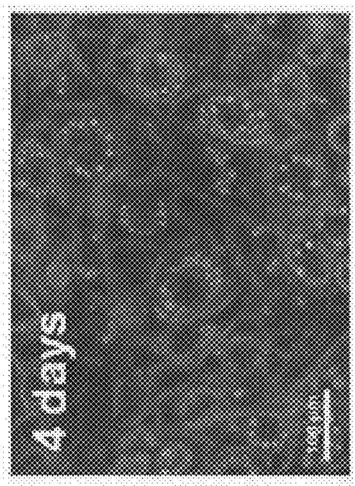
FIG. 1C shows the cellular morphology of cultured 3T3-L1 pre-adipocytes on day 4.
Figure 1D:
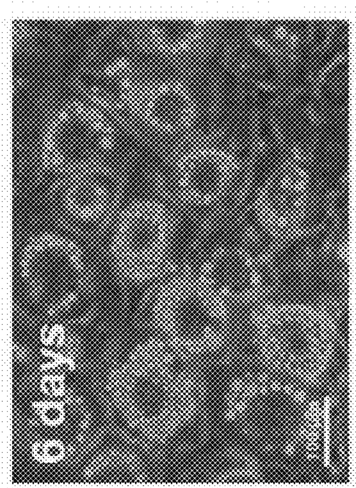
FIG. 1D shows the cellular morphology of cultured 3T3-L1 pre-adipocytes on day 6.
Figure 1E:
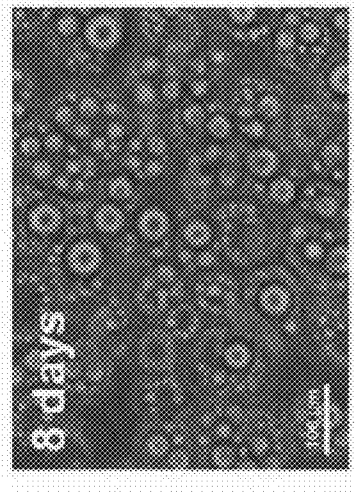
FIG. 1E shows the cellular morphology of cultured 3T3-L1 pre-adipocytes on day 8.
Figure 1F:
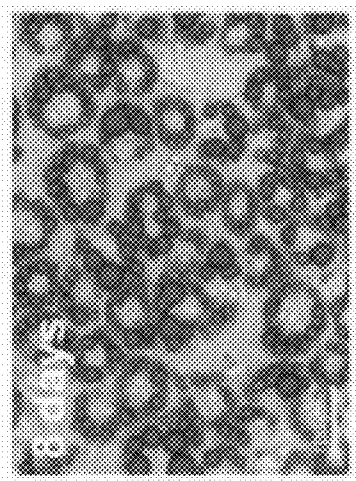
FIG. 1F shows the oil red staining of cultured 3T3-L1 pre-adipocytes on day 8.

The present invention discloses a HPMFs compound for inhibiting lipogenesis, suppressing adipocyte differentiation and preventing lipid accumulation. The HPMFs compound and/or derivatives thereof with an effective dosage could be used as an active ingredient of a composition for treating or preventing obesity-related diseases. Moreover, the HPMFs compound is extracted from a peel of genus *citrus*. By administering to a subject the composition, it is helpful for suppression of adipocyte differentiation and decrease of adipocyte accumulation.

Furthermore, the HPMFs compound is generated from polymethoxylflavones (PMFs) by replacing at least one methoxyl- group (—OCH3) by hydroxyl- group (—OH).

The previous studies have indicated that differentiation process from 3T3-L1 pre-adipocytes to the mature adipocytes is mediated by various signaling pathways. For example, the lipogenesis promoting transcription factors such as PPAR and C/EBPs are capable of triggering the maturation of 3T3-L1 pre-adipocytes. Herein, c/EBPs can activate the downstream target that involves in lipid metabolism such as fatty acid binding protein 2 (hereinafter referred to as aP2). In addition, SREBP-1 is the critical factor for cell fate determination of adipocyte differentiation through activating downstream targets involving in lipogenesis such as fatty acid synthase (hereinafter referred to as FAS) and acetyl-CoA carboxylase (hereinafter referred to as ACC). Therefore, activation of the target of SREBP-1 is capable of accelerating the synthesis of fatty acid and lipid, and activation of PPARγ. Moreover, LKB1/STK11 activates AMPKα through phosphorylation on Thr172 of AMPKα to further suppress the activity of ACC and inhibit lipogenesis. Therefore, regulation of Adenosine monophosphate-activated protein kinase (hereinafter referred to as AMPK) is the critical indicator for anti-lipogenesis.

The HPMFs compound is capable of controlling the expressions of transcription factors and the related signaling pathways that participate in regulation of adipocyte differentiation. Therefore, the HPMFs can suppress differentiation and maturation of adipocytes. In detail, the HPMFs compound is capable of suppressing the critical transcription factors for adipocyte differentiation such as PPARγ and C/EBPα. Furthermore, the HPMFs compound can inhibit the protein synthesis of the downstream targets such as ACC, FAS and aP2 to slow down the accumulation of triglyceride. In addition, activation of AMPK pathway and suppression of PI3K/AKT pathway are capable of inhibiting the adipocyte differentiation.

Unless defined otherwise, all technical and scientific terms used herein have the same meanings commonly understood by one of ordinary skill in the art. As used in this application, including claims and specification, the following words is only exemplary and illustrative, not limiting in scope.

The term of composition is including, but not limiting to, a pharmaceutical composition and a dietary supplement, wherein the pharmaceutical composition comprises an active ingredient and one or more pharmaceutically acceptable carriers or excipients. According the invention, the active ingredient is the HPMFs compound or a pharmaceutically acceptable salt thereof, or mixture thereof. Moreover, the pharmaceutical composition is in the form of granular, powder, pastille, capsule, suppository, liquid, suspension, drop or the solvent for injection. The dietary supplement is a functional food in the form of granular, powder, solid substance, liquid, suspension or semi-solid substance.

The term of pharmaceutically acceptable salt refers to the salt or free form of the acidic or basic product produced from the HPMFs, wherein the HPMFs and stereoisomers thereof are both capable of forming the salt.

The term of effective dose refers to the amount or dose of a compound or a composition that is sufficient to produce an effective response upon administration to a mammal by calculation according to the races, body weight and delivery methods.

The term of administering refers to a delivery method that includes oral intake, breath intake, colon absorption, epidermal absorption, subcutaneous injection, artery injection, venous injection or intra-peritoneal injection.

The term of a or an refers to one or more than one.

To understand the purposes and advantages of the present invention, it is described by the following merely examples taken in conjunction with the accompanying drawings. It will be understood that it is not intended to limit the invention to the described embodiments.

Example 1

Preparation of the HPMFs Compound 10 grams of orange peel extract that contained HPMFs for more than 40% was dissolved in 95% ethanol and added with 3M of hydrochloric acid (HCl). The indicated mixture was incubated with heating circumfluence and monitored by using TLC and LC/MS for 12 hours. Until the reaction finished and cooled, ethanol was removed by vacuum device. In the following step, ethyl acetate and water were added for separation and extraction. An organic solvent phase of the extract was collected, first. The remained aqueous phase was further extract by acetyl acetate again for isolating the organic solvent phase.

The organic solvent phases were pulled together, diluted with sodium bicarbonate solution, water and 30% NaCl solution for wash, and then dehydrated with sodium sulfate. After filtration, decompression concentration and lyophilized, the gained pale yellow solid substance is a HPMFs compound.

Example 2

Culture of 3T3-L1 Pre-Adipocytes

The 3T3-L1 pre-adipocytes were cultured in 10 cm culture dish with DMEM medium, which contains 10% fetal bovine serum (FBS), 10000 unit/mL of penicillium and 10000 μg/mL streptomycin, at 37° C., 5% CO2, incubator. When the growing cells occupied 70%-80% area of the cultured dish, depletion of cultured medium was followed by PBS washing. The cultured cells were added trypsin-EDTA at 37° C. After the enzymatic digestion, the cultured cells were disassociated from the dish by gentle beats and then adding fresh FBS-containing medium to terminate the enzymatic activity of trypsin-EDTA. The disassociated cells were further well separated by pipetting using pipetman several times. The cells were evenly distributed in the culture dishes and then incubated at 37° C., 5% CO2 incubator.

Example 3

Differentiation Test of 3T3-L1 Pre-Adipocytes

The 3T3-L1 pre-adipocytes seeded into 24-wells plate were cultured in FBS-containing DMEM medium for 3 days. In the following step, the original medium was replaced by another fresh FBS-containing medium for 2 days extension culture. The day after 2 days extension culture is destined as the "day 0".

On day 0, the 3T3-L1 pre-adipocytes cultured with different conditions were treated with DMI inductance (DEX+MIX+insulin) for 2 days (day 2) to induce the adipocyte differentiation. After the induction of adipocyte differentiation, the induction medium was replaced by a fresh DMEM medium that contains 10% FBS and 5 μg/mL INS for at least 2 days culture (day 4). On day 4, day 6 and day 8, the culture medium was further replaced by the new 10% FBS-containing DMEM medium.

During the culture from day 0 to day 8, the morphology of the 3T3-L1 pre-adipocytes was observed every 2 days and the results were shown in FIG. 1A~1E. In addition, the Oil-red O staining of the 3T3-L1 pre-adipocyte on day 8 was shown in FIG. 1F. The red spots in the staining indicate the lipid-drops in adipocyte. The results in FIG. 1 show that the morphology of the undifferentiated 3T3-L1 pre-adipocyte is spindle shape. On day 2, some cultured 3T3-L1 pre-adipocytes switch their morphology into round shape. On day 4, some small lipid-drops are appeared in the cultured 3T3-L1 pre-adipocytes. On day 6, the accumulated lipid-drops in the cultured cells are increased. On day 8, the cultured 3T3-L1 pre-adipocyte differentiate into the mature adipocytes that are present with accumulation of the lipid-drops.

Example 4

Analysis of Lipid Accumulation in 3T3-L1 Pre-Adipocyte

The cultured 3T3-L1 pre-adipocytes on day 8 prepared in example 3 were divided into 4 groups and cultured with different conditions. Herein, the group 1 was the blank control treated without additional factors, the group 2 was treated with DMI containing medium on day 2 as the control group, the group 3 was treated not only MDI on day 2, but also added with 10 μg/mL the HPMFs compound on day 0, day 2, day 4, and day 6 and the group 4 was treated not only MDI on day 2, but also added with 20 μg/mL the HPMFs compound on day 0, day 2, day 4, and day 6.

Figure 2A:
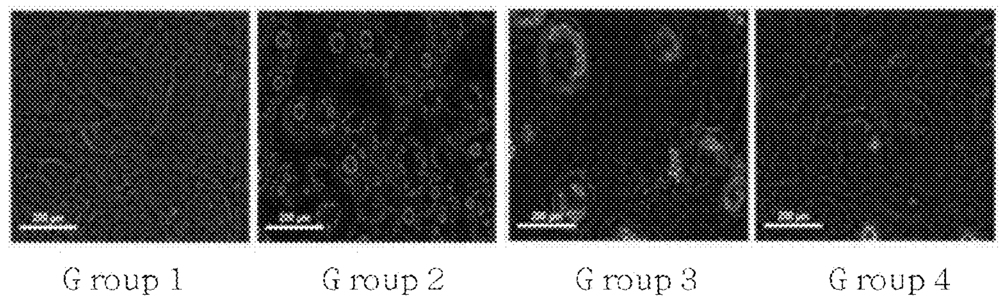
FIG. 2A~2B show the oil red staining of cultured 3T3-L1 pre-adipocytes with different treatments on day 8 after differentiation.
Figure 2B:
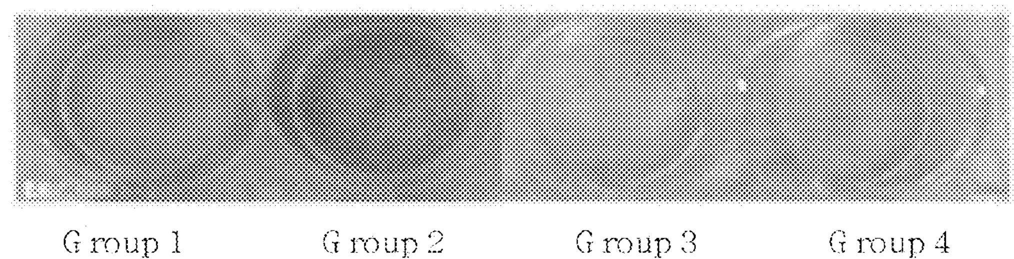
Figure 2C:
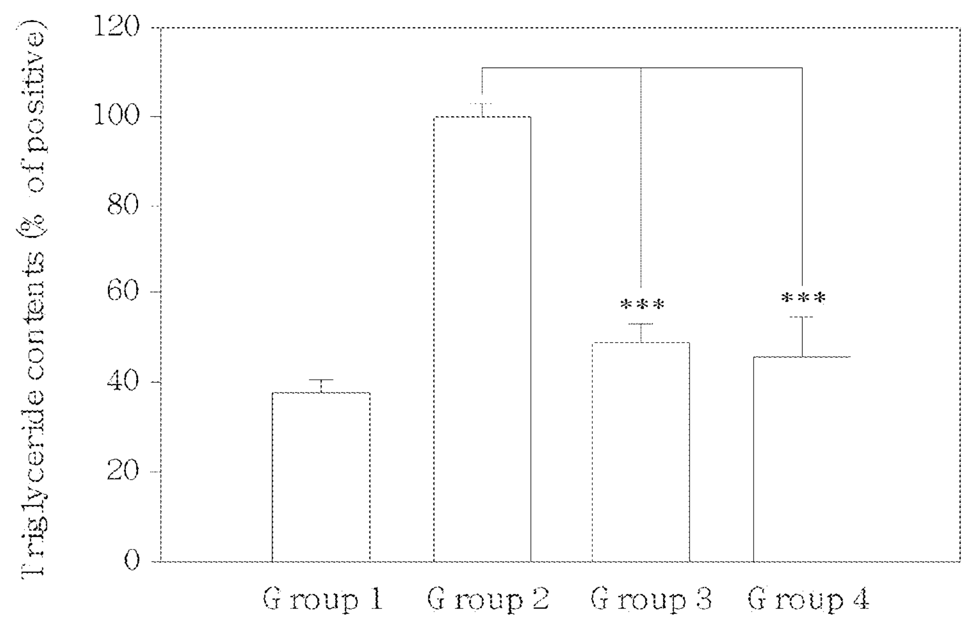
FIG. 2C shows the content of triglyceride in cultured 3T3-L1 pre-adipocytes with different treatments on day 8 after differentiation.

After the complete culture on day 8, the each group stained by Oil Red O staining was observed and recorded by photograph under microscope. The morphology of the Oil Red O stained cells of the each group was shown in FIGS. 2A and 2B. Furthermore, the lipid content of the each group was measured by spectrophotometer 510 nm and shown in FIG. 2C.

According to FIG. 2, the group 1 is the un-differentiated 3T3-L1 pre-adipocytes and the morphology thereof are spindle shape. In the group 2, the 3T3-L1 pre-adipocytes differentiate into mature adipocyte bearing round shape and have the red lipid-drops therein. In contrast to the group 2, the 3T3-L1 pre-adipocytes in the group 3 and 4 reveal extremely less red lipid-drops, respectively. The results indicate the function of the HPMFs compound in suppressing the lipogenesis induced by DMI-induced 3T3-L1 pre-adipocytes. Therefore, it shows that treatment of the HPMFs compound on the 3T3-L1 pre-adipocytes reduces the lipid content and significantly inhibits the lipid accumulation in the cells.

Example 5

Analysis the Mechanism of the HPMFs Compound Inhibiting Lipogenesis

The cultured 3T3-L1 pre-adipocytes on day 8 prepared in example 3 were divided into 4 groups and cultured with different conditions. Herein, the group 1 was the blank control, the group 2 was treated with DMI-containing medium on day 2 as the control group, the group 3 was added not only MDI on day 2 but also 10 μg/mL HPMFs on day 0, day 2, day 4, and day 6, respectively and the group 4 was added not only MDI on day 2 but also 20 μg/mL HPMFs on day 0, day 2, day 4, and day 6.

Figure 3A:
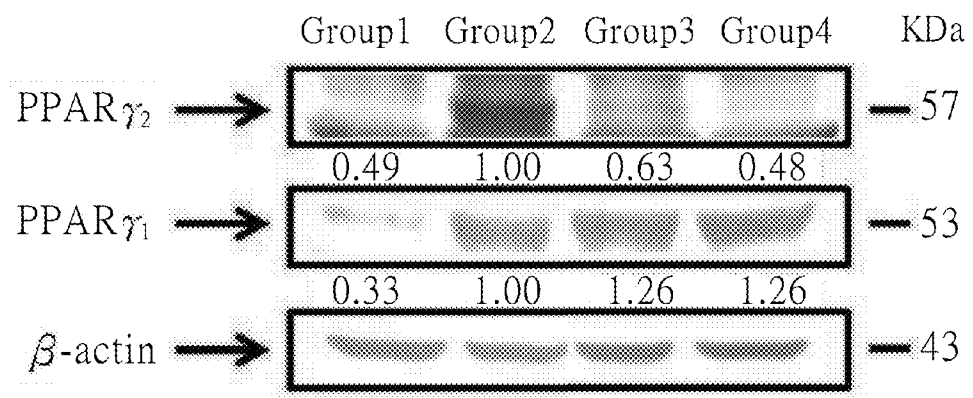
FIG. 3A shows the expression level of PPARγ in cultured 3T3-L1 pre-adipocytes with different treatments on day 8 after differentiation.
Figure 3B:
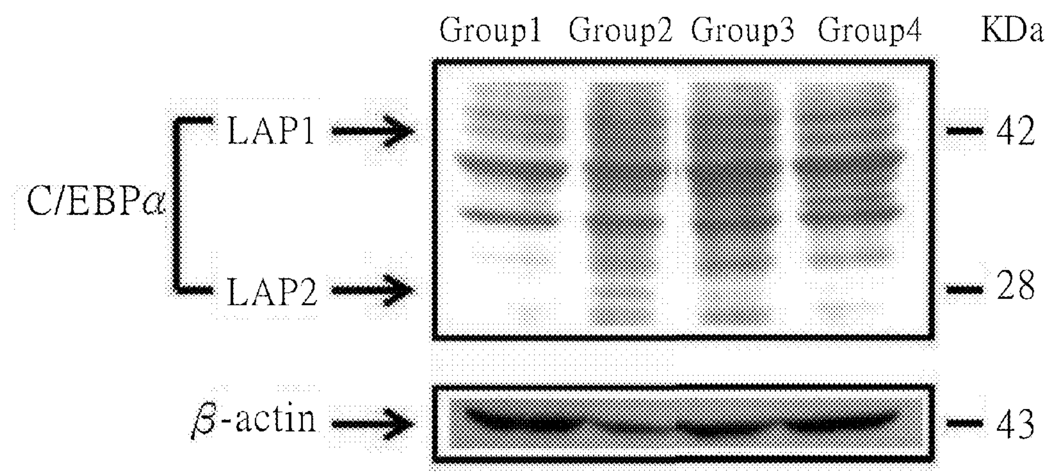
FIG. 3B shows the expression level of C/EBPα in cultured 3T3-L1 pre-adipocytes with different treatments on day 8 after differentiation.
Figure 4A:
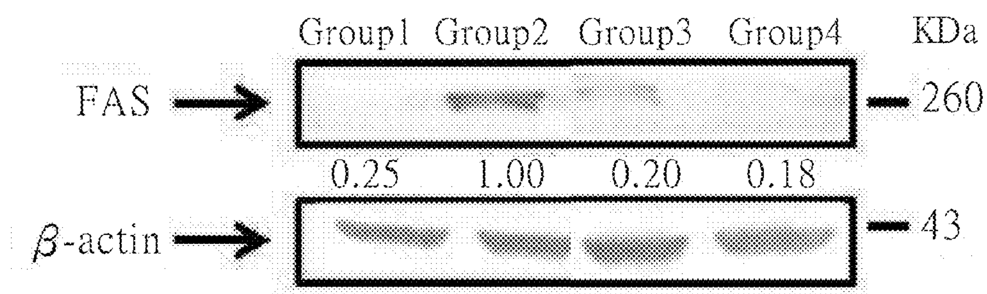
FIG. 4A shows the expression level of fatty acid synthase in cultured 3T3-L1 pre-adipocytes with different treatments on day 8 after differentiation.
Figure 4B:
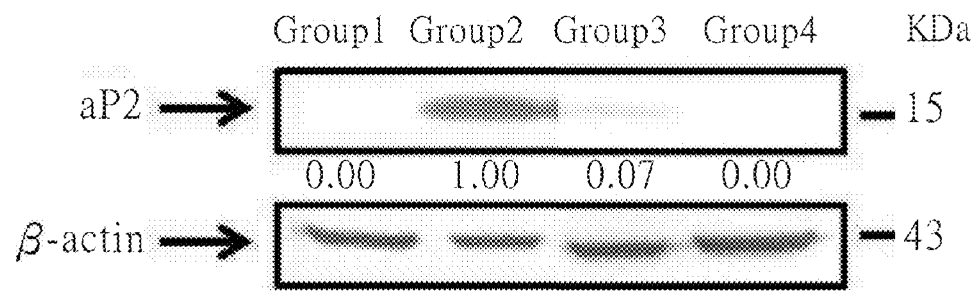
FIG. 4B shows the expression level of fatty acid binding protein 2 (aP2) in cultured 3T3-L1 pre-adipocytes with different treatments on day 8 after differentiation.
Figure 4C:
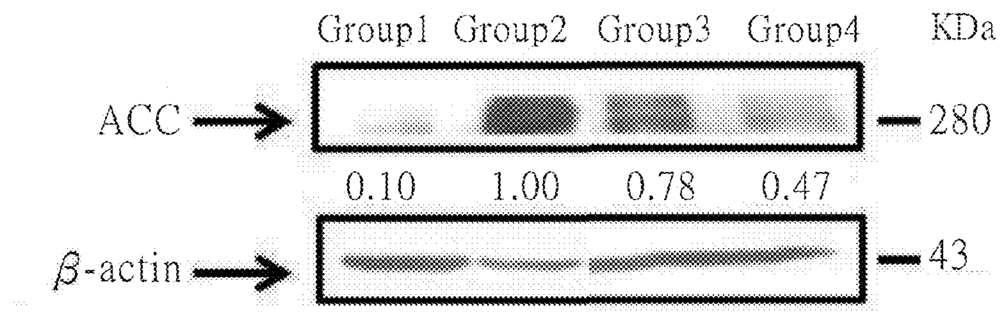
FIG. 4C shows the expression level of acetyl-coA carboxylase in cultured 3T3-L1 pre-adipocytes with different treatments on day 8 after differentiation.
Figure 5A:
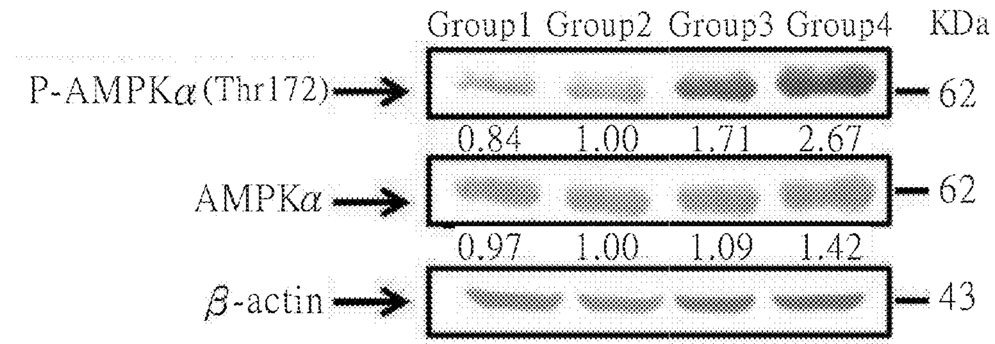
FIG. 5A shows the expression levels of AMP-activated protein kinase-α (AMPK-α) and phospho-AMPK-α (Thr172) in cultured 3T3-L1 pre-adipocytes with different treatments on day 8 after differentiation.
Figure 5B:
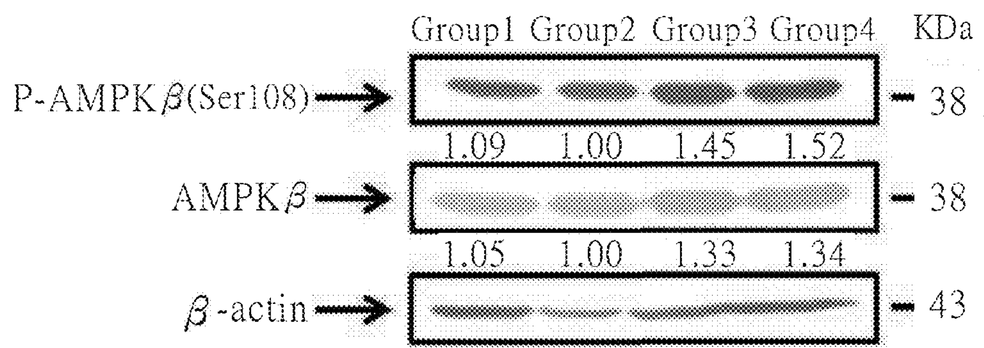
FIG. 5B shows the expression levels of AMP-activated protein kinase-β (AMPK-β) and phospho-AMPK-β (Ser108) in cultured 3T3-L1 pre-adipocytes with different treatments on day 8 after differentiation.
Figure 5C:
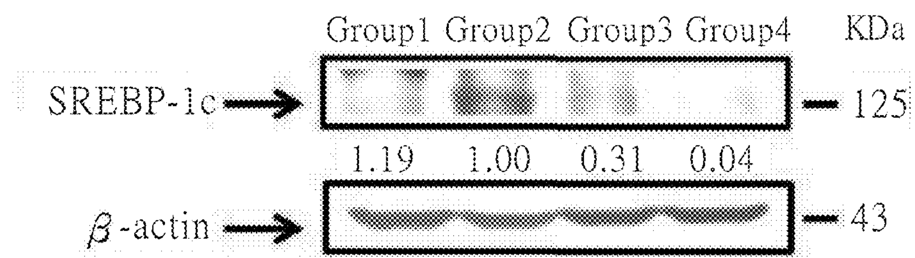
FIG. 5C shows the expression level of sterol regulatory element binding protein 1c (SREBP 1c) in cultured 3T3-L1 pre-adipocytes with different treatments on day 8 after differentiation.

The cell lysate of the each group was collected to determine the protein expression by western blot analysis. The results were present in FIG. 3 to FIG. 5, wherein FIG. 3A shows the expression of PPARγ in the each group, FIG. 3B shows the expression of C/EBPα in the each group, FIG. 4A shows the expression of FAS in the each group, FIG. 4B shows the expression of aP2 in the each group, FIG. 4C shows the expression of ACC in the each group, FIG. 5A shows the expression of AMPKα and p-AMPKα (Thr172) in the each group, FIG. 5B shows the expressions of AMPK-β and p-AMPK-β (Ser108) in the each group and FIG. 5C shows the expression of SREBP-1c in the each group.

Furthermore, the cultured 3T3-L1 pre-adipocytes on day 8 prepared in example 3 were divided into three groups, wherein the group 1 was the blank control, the group 2 treated with DMI on day 2 was positive control and the group 3 was treated with DMI on day 2 and administrated with 20 μg/mL HPMFs on day 0, day 2, day 4, and day 6. After the induction culture, the cells of the each group were collected and lysed for analysis of gene expression by western blot. The results were shown in FIG. 6 that includes the expressions of PI3K, p-PI3K (Tyr508), AKT and p-Akt (Ser473) in the each groups.

According to FIG. 3 and FIG. 4, it suggests that the expression levels of PPARγ, C/EBPα, ACC, FAS and aP2 in the group 2 are increased with comparison of the group 1. In contrast, treatments of the HPMFs compound in group 3 and group 4 resulted in the decreased expression levels of PPARγ, C/EBPα, ACC, FAS and aP2 with comparison of the group 2.

Figure 6:
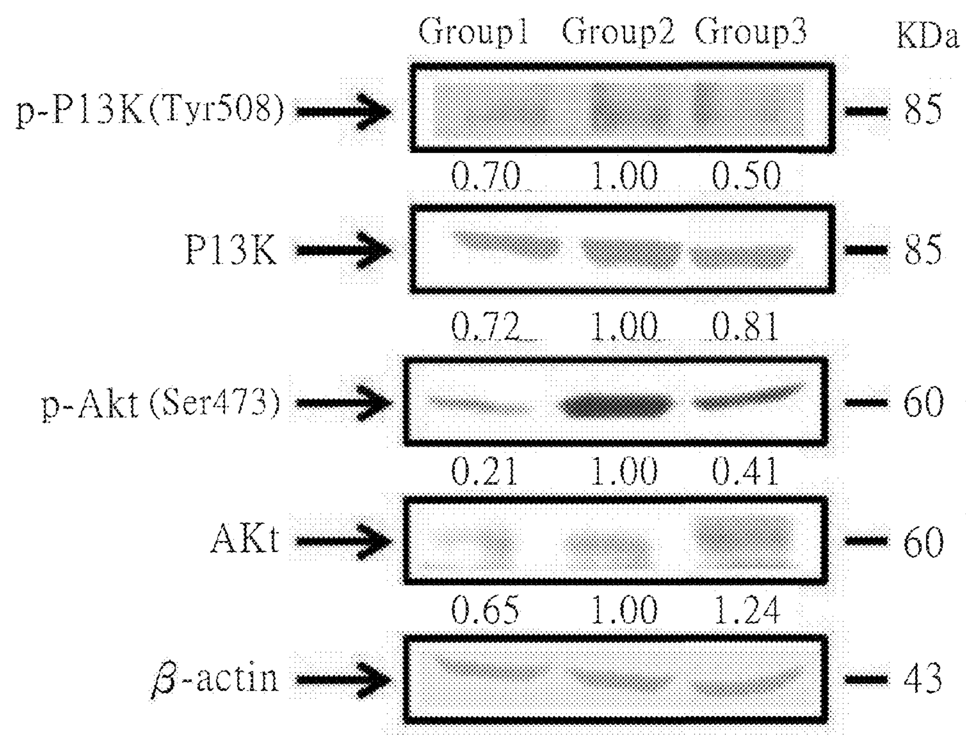
FIG. 6 shows the expression levels of PI3K, phospho-PI3K (Tyr508), AKT and phospho-AKT (Ser473) in cultured 3T3-L1 pre-adipocytes with different treatments on day 8 after differentiation.

According to FIG. 5, it shows that there is no significant difference in the expression levels of p-AMPKα (Thr172) and p-AMPKβ (Ser108) between the group 1 and the group 2. Comparing with the group 2, the expression levels of p-AMPKα (Thr172) and p-AMPKβ (Ser108) in the group 3 or the group 4 are increased and the expression levels of SREBP1c in the group 3 or the group 4 are decreased. Moreover, the higher concentration of the HPMFs compound was treated, the more p-AMPKα (Thr172) and p-AMPKβ (Ser108) will be express. As shown in FIG. 6, the expression levels of p-PI3K(Tyr508) and p-AKT(Ser473) in the group 2 are increased with comparison of the group 1, and the expression levels of p-PI3K(Tyr508) and p-AKT(Ser473) in the group 3 are decreased with comparison of the group 2.

The results in FIG. 3 to FIG. 6 suggest that the HPMFs compound is capable of suppressing the expression of transcription factor required for adipocyte differentiation such as PPARγ, C/EBPα and their downstream proteins including ACC, FAS and aP2. In addition, treatment of the HPMFs compound activates AMPK signaling pathway through phosphorylation on AMPKα (Thr172) and AMPKβ (Ser108). In contrast, treatment of the HPMFs compound suppresses expression level of PPARγ through reducing the protein level of SREBP-1c. In addition, treatment of the HPMFs compound suppresses PI3K/AKT signaling pathway through suppresses the phosphorylation on PI3K (Tyr508) and AKT (Ser473). Therefore, it shows that the effects of the HPMFs compound in controlling gene expression profile and modulating the molecular signaling pathway are capable of preventing the maturation of 3T3-L1 pre-adipocytes.

Example 6

The Cell Cycle Analysis of 3T3-L1 Pre-Adipocytes

The 3T3-L1 pre-adipocytes passaged in 24-wells plate were cultured with FBS-containing DMEM for 3 days. In the next step, the cells were cultured with fresh FBS-containing DMEM medium for 2 days. The day after the indicated culture procedure for 5 days was destined as "day 0". In the following steps, the cells were grouped and treated with different culture conditions, wherein the group 1 was the blank control, the group 2 was the control group treated with DMI on day 2, the group 3 was treated with DMI-containing medium and added 10 μg/mL of the HPMFs compound on day 2 and the group 4 was treated with DMI-containing medium and added 20 μg/mL of the HPMFs compound on day 2.

The cultured cells in the each group were fixed for propidium iodide (hereinafter referred to as PI) staining on 18 and 24 hour. The PI-stained cells in the each group were further analyzed by flow cytometry and software (ModFit LT) to determine the cells cycle progression. The results of cell cycle analysis were showed in FIG. 7A, 7B and table 1.

TABLE 1

Distribution of cell cycle progression of each group on different time points

| Time points | Groups | Phases of cell cycle (%). G0/G1 | S | G2/M |
|---|---|---|---|---|
| 18 hours | 1 | 76.72 ± 1.13 | 15.36 ± 3.27 | 7.60 ± 2.41 |
| | 2 | 27.61 ± 1.63 | 71.89 ± 1.65 | 0.50 ± 0.53 |
| | 3 | 70.08 ± 1.64 | 29.64 ± 2.03 | 0.04 ± 0.05 |
| | 4 | 83.66 ± 0.56 | 12.21 ± 0.27 | 5.22 ± 0.82 |
| 24 hours | 1 | 77.05 ± 0.89 | 13.96 ± 0.27 | 8.59 ± 0.75 |
| | 2 | 49.13 ± 1.35 | 15.40 ± 0.24 | 35.47 ± 1.12 |
| | 3 | 30.67 ± 0.88 | 48.87 ± 1.44 | 10.17 ± 0.19 |
| | 4 | 82.59 ± 0.44 | 12.57 ± 1.04 | 4.84 ± 1.48 |

Figure 7A:
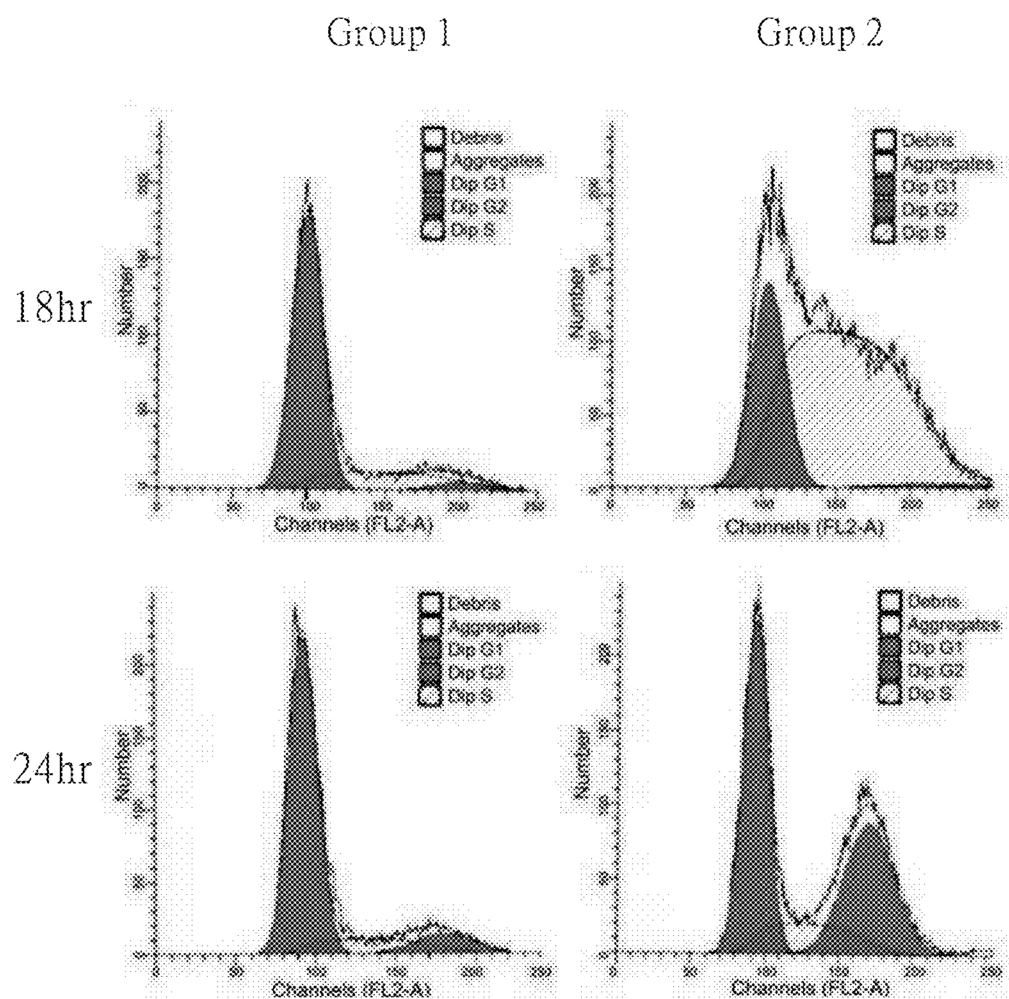
FIG. 7A~7B shows the cell cycle analysis of cultured 3T3-L1 pre-adipocytes with different treatments.
Figure 7B:
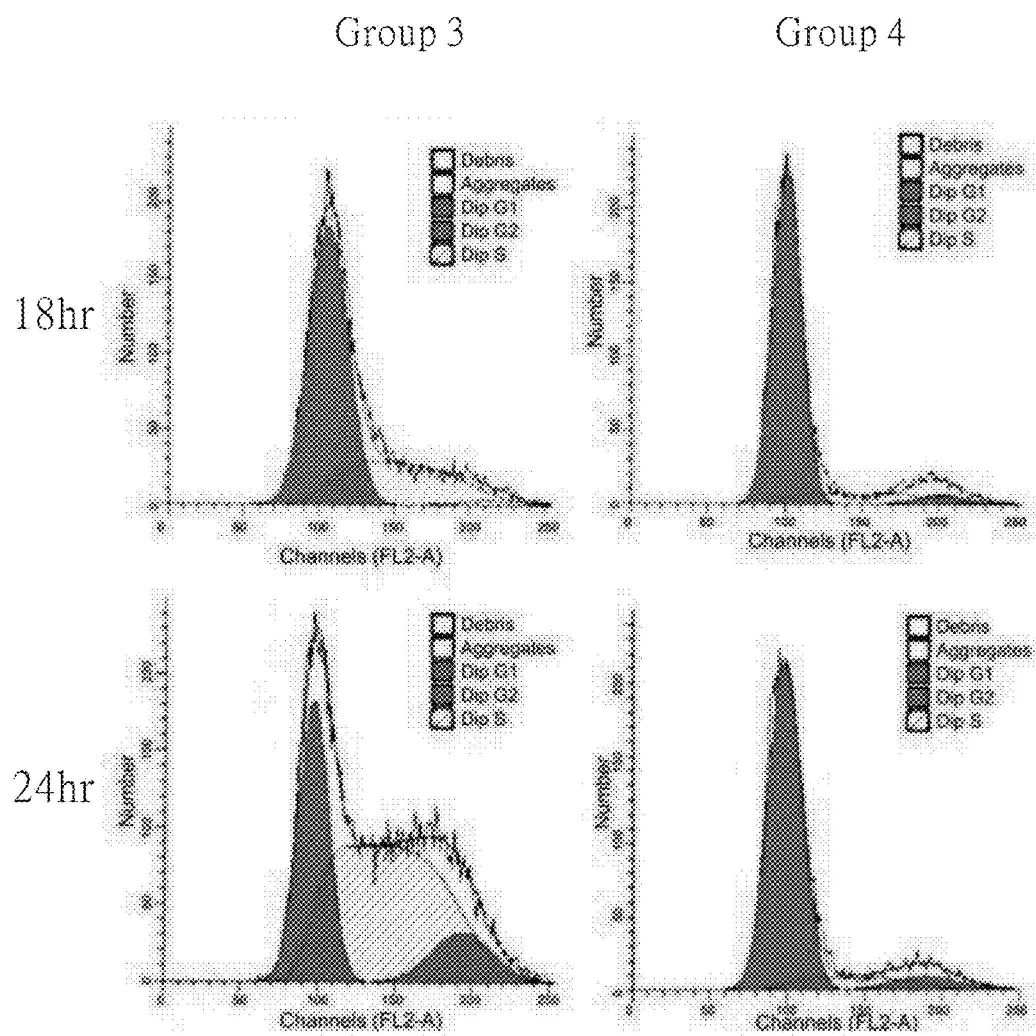

As shown in FIG. 7A, 7B and table 1, after treating for 18 hours, there are 76.72% of the cultured 3T3-l1 pre-adipocytes in the group 1 into G0/G1 phase and only 15.36% of the cultured 3T3-L1 pre-adipocytes in the group 1 progressing into S phase, 71.89% of the cultured 3T3-L1 pre-adipocytes in the group 2 into S phase, 29.64% of the cultured 3T3-L1 pre-adipocytes in the group 3 into S phase and 12.21% of the cultured 3T3-L1 pre-adipocytes in the group 4 into S phase. Furthermore, after treating for 24 hours, the cultured 3T3-L1 pre-adipocytes in the group 1 all retain in G0/G1 phase, 35.47% of the 3T3-L1 pre-adipocyte in the group 2 progress into G2/M phase, 10.17% of the 3T3-L1 pre-adipocyte in the group 3 are into G2/M phase and 4.84% of the 3T3-L1 pre-adipocyte in the group 4 progress to G2/M phase.

According to the results in FIG. 7, it indicates that treatment of DMI on 3T3-L1 pre-adipocyte will induce mitotic clonal expansion, however, the HPMFs compound will decrease the mitotic clonal expansion and retain the cells in G0/G1 phases to prevent post-mitotic adipocyte differentiation and lipogenesis.

Example 7

Preparation of Obesity Mouse Model

Figure 8:
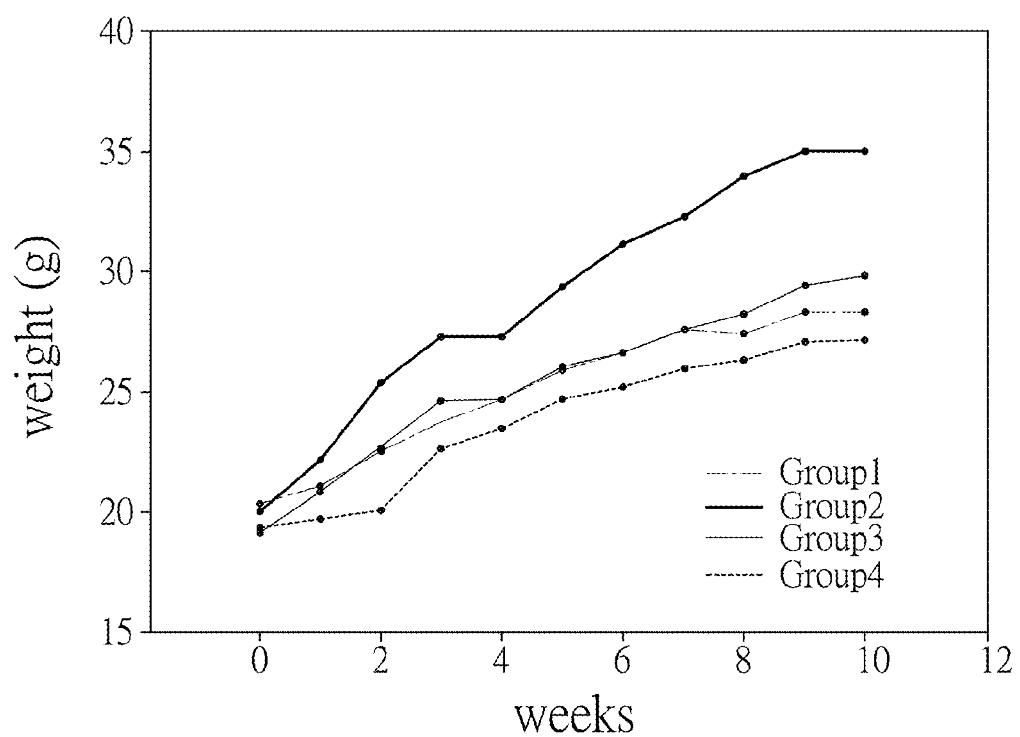
FIG. 8 shows the changes in the body weights of the each group mice with different administrations.
Figure 9:
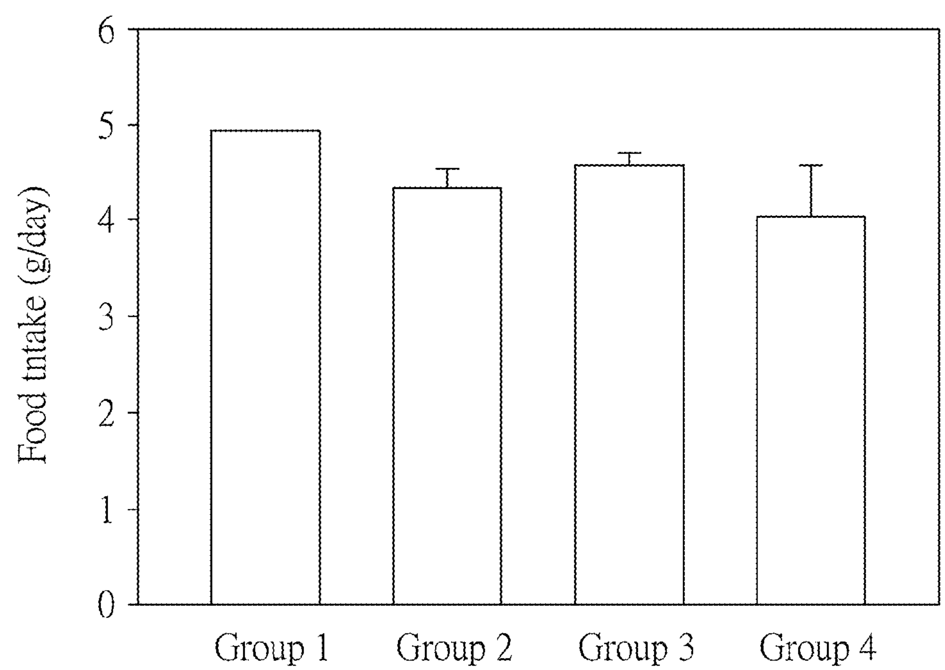
FIG. 9 shows the dietary intakes of the each group mice with different administrations.
Figure 11A:
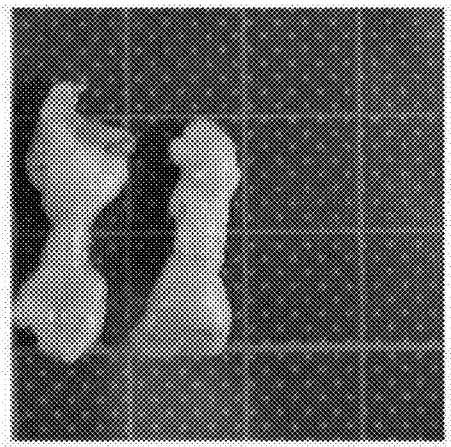
FIG. 11A~11D show the gross views of the fat pads surrounding gonad of the each group mice with different administrations.
Figure 11B:
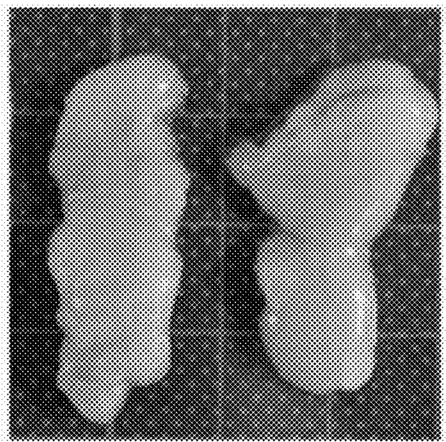
Figure 11C:
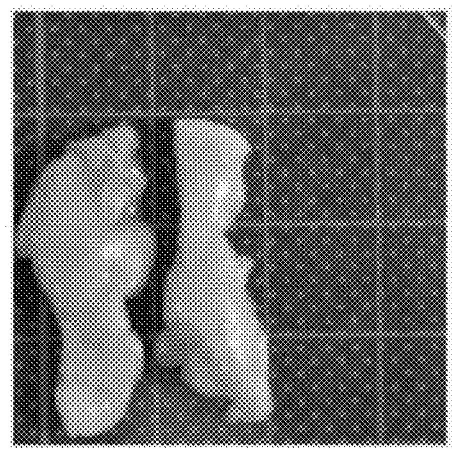
Figure 11D:
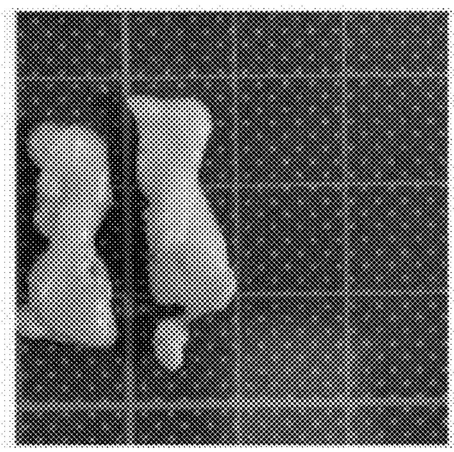
Figure 12A:
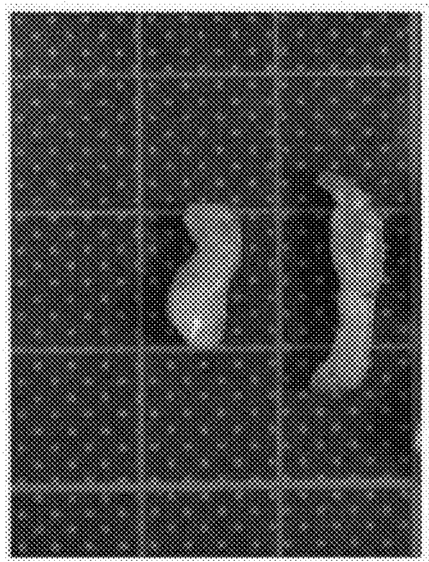
FIG. 12A~12D show the gross views of the abdominal fat pads of the each group mice with different administrations.
Figure 12B:
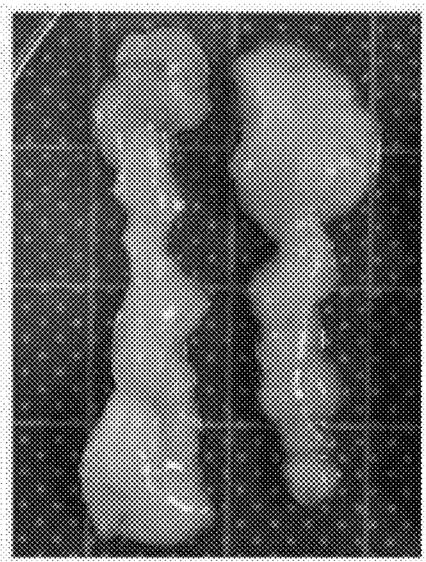
Figure 12C:
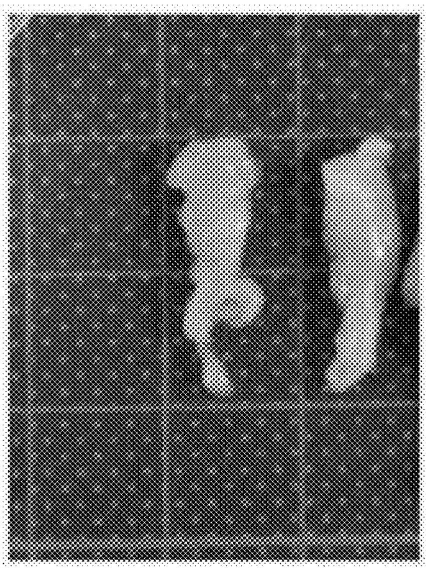
Figure 12D:
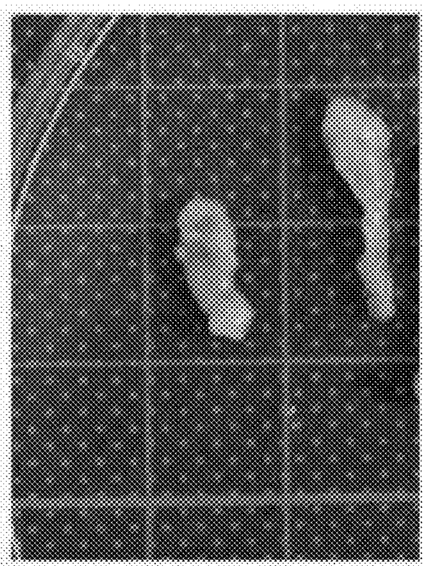

The 4 weeks-old male C57BL/6 mice were divided into 4 groups and treated with different feeding conditions, wherein the group 1 was the blank control fed with normal diet and water, the group 2 was fed with high-fat diet and water the group 3 was fed with high-fat diet, water and 250 mg/Kg the HPMFs compound, and the group 4 was fed with high-fat diet, water and 10 g/Kg the HPMFs compound. Feeding for 10 weeks, the body weights of the mice in the each group were monitored every week as shown in FIG. 8 and the dietary intakes of the mice in the each groups were statistically recorded as shown in FIG. 9. In addition, the gross views of the mice in the each group were shown in FIG. 10A~10D.

The results shown in FIG. 8 to FIG. 10 indicate that the dietary intakes recorded from week 0 to week 10 are similar between the four groups. Observing the change of body weight in the each group, the mice of the group 1 are from 20.27 g to 28.31 g, the mice of the group 2 are from 19.93 g to 35.11 g, the mice of the group 3 are from 19.15 g to 27.18 g and the mice of the group 4 are from 19.32 g to 27.18 g.

Consistent with the body weights, the mice in the group 2 reveals obviously larger body size than the mice in the group 1 after conditional feeding for 10 weeks. The gross view of the mice in the group 3 or in the group 4 reveal smaller size than that in the group 2, furthermore, the gross view of the mice in the group 4 are similar than that in the group 1.

Therefore, it shows that feeding with high-fat diet is capable of preparing the mouse model of obesity. In addition, it can prevent the body weight of obesity mouse to increase by oral feeding with the HPMFs compound. In other words, it suggests that the HPMFs compound is able to inhibit the increase of body weight without changing dietary intakes.

Example 8

Analyzing Weights of Internal Organs of the Mice in the Each Group

The mice in the each group of example 7 were sacrificed for dissection. The weights of liver, kidney and spleen of the mice in the each group were measured and recorded in table 2.

TABLE 2

| Weights of internal organs collected from the mice in the each group | | | | |
|---|---|---|---|---|
| Organ | Group 1 | Group 2 | Group 3 | Group 4 |
| Liver | 1.14 ± 0.17 | 1.47 ± 0.07 | 1.30 ± 0.16 | 1.23 ± 0.08 |
| Kidney | 0.45 ± 0.02 | 0.54 ± 0.05 | 0.44 ± 0.05 | 0.40 ± 0.03 |
| Spleen | 0.06 ± 0.01 | 0.07 ± 0.01 | 0.07 ± 0.02 | 0.07 ± 0.01 |

In Table 2, the weights of liver and kidney in the group 2 increasing 0.33 g and 0.06 g with the comparison of group 1, respectively. It suggests that the excessive accumulation of fat results in the increased weight of the internal organs. Comparing with the group 2, the weights of the liver and kidney in the group 3 decrease 0.17 g and 0.10 g, respectively and that in the group 4 decrease 0.24 g and 0.14 g, respectively.

According to the results in table 2, it shows that administering the HPMFs compound will inhibit the lipid accumulation in internal organs decrease and the effect will be better with administering more the HPMFs compound. Furthermore, because the weights of the spleen between the four groups are similar, it indicates that the HPMFs compound doesn't have the cell toxicity.

Example 9

Analysis of the Internal Fat of Mice in the Each Group

After sacrificed the mice of the each group in example 7, the fat pads surrounding gonads, abdomen and intestine of the mice in the each group were be observed as shown were in FIG. 11 and FIG. 12, wherein FIGS. 11A to 11D were sequentially the gross views of the fat pads surrounding gonad in the group 1 to 4, and FIG. 12A to 12D were sequentially the gross views of the abdominal fat pads in the group 1 to 4. Furthermore, measuring the weights of the fat pads surrounding gonads, abdomen and intestine collected from the mice in the each group, the results were shown below:

The weights of the fat pads surrounding gonad, abdomen and intestine in the group 1 were 0.60 g, 0.06 g and 0.34 g, respectively. The weights of the fat pads surrounding gonad, abdomen and intestine in the group 2 were 1.65 g, 0.56 g and 0.67 g, respectively. The weights of the fat pads surrounding gonad, abdomen and intestine in the group 3 were 0.79 g, 0.21 g and 0.39 g, respectively. The weights of the fat pads surrounding gonad, abdomen and intestine in the group 4 were 0.42 g, 0.06 g and 0.27 g, respectively. These weights of the internal fat pads in the four groups were further statistical analysis and shown in FIG. 13 to FIG. 15, wherein FIG. 13 shows the results of the weights of the fat pads surrounding gonad in the each group, FIG. 14 shows the results of the weights of the fat pads surrounding abdomen in the each group and FIG. 15 shows the results of the weights of the fat pads surrounding intestine in the each group.

According to FIG. 11 and FIG. 12, it suggests that the gross views of the fat pads surrounding gonad and abdomen in the group 2 are obviously larger than that in the group 1. Comparing with the group 2, the gross views of the fat pads surrounding gonad and abdomen in the group 3 and 4 were obviously reduced size.

Figure 13:
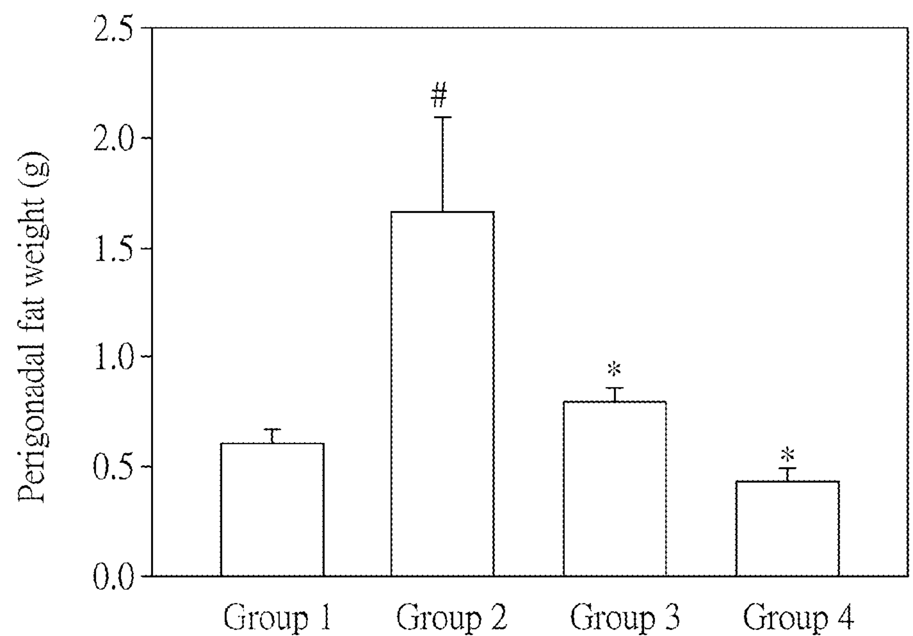
FIG. 13 shows the weights of the fat pads surrounding the gonad of the each group mice with different administrations.
Figure 14:
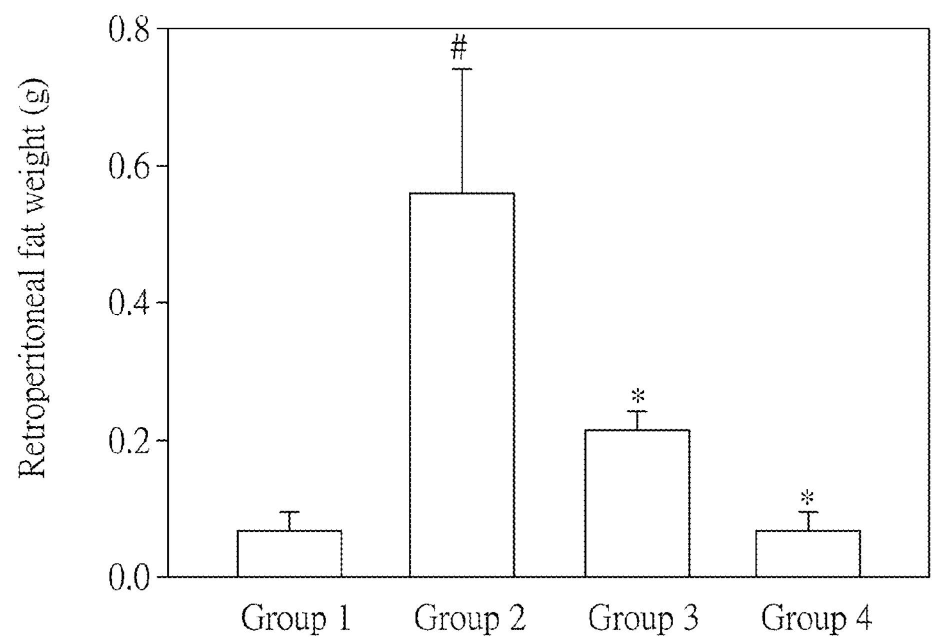
FIG. 14 shows the weights of the abdominal fat pads of the each group mice with different administrations.
Figure 15:
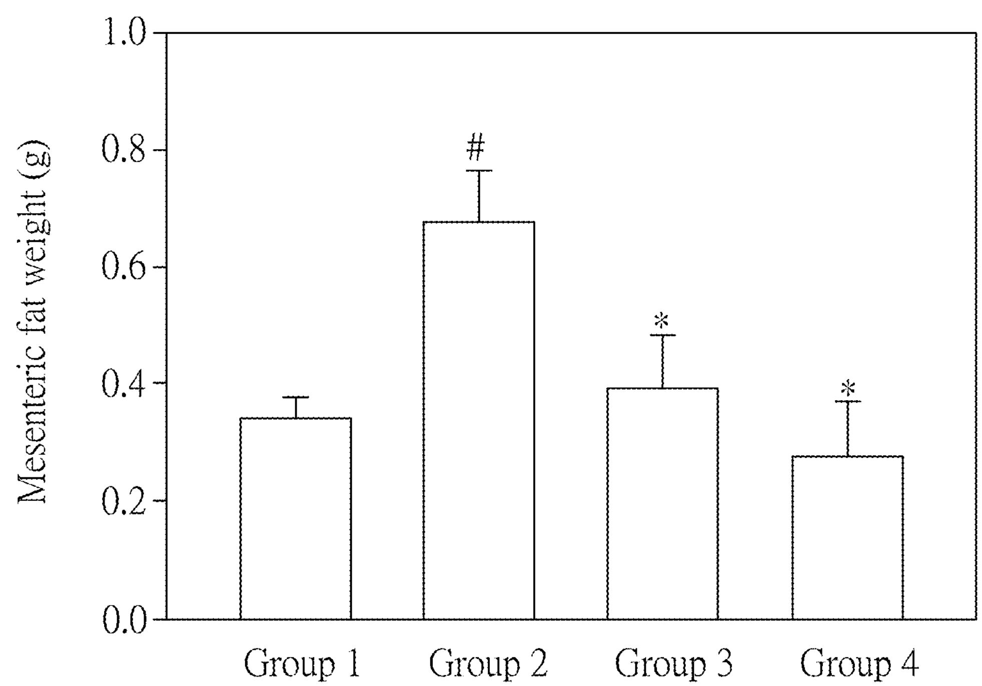
FIG. 15 shows the fat pads surrounding intestine of the mice in the each group with different administrations.
Figure 16A:
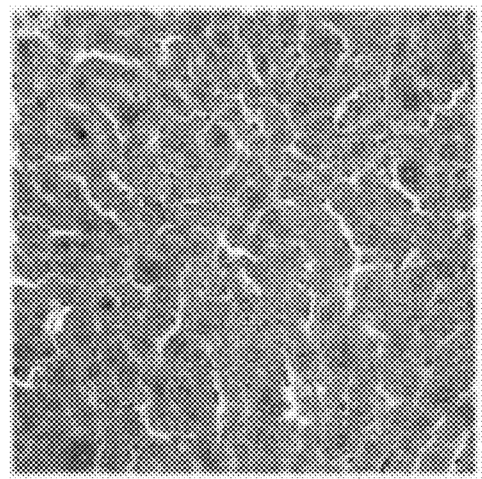
FIG. 16A~16D show H&E staining for hepatic histology of the each group mice with different administrations.
Figure 16B:
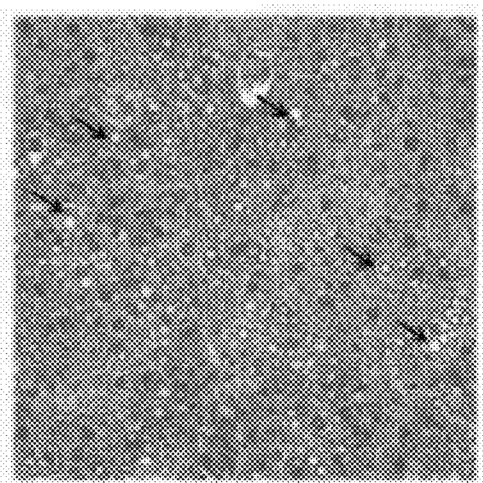
Figure 16C:
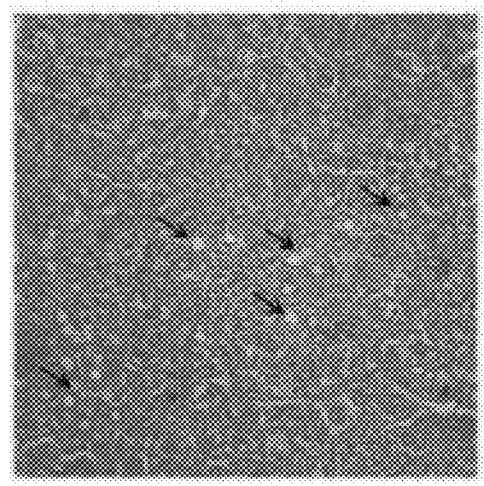
Figure 16D:
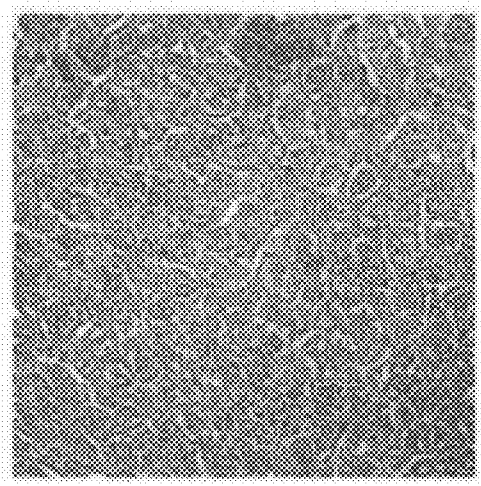

Furthermore, the results in FIG. 13 and FIG. 14 show the increases of 1.05 g, 0.50 g and 0.33 g on the fat pads surrounding gonad, abdomen and intestine of the group 2 with comparison of the group 1, respectively. And comparing with the group 2, the weights of the fat pads surrounding gonad, abdomen and intestine of the group 3 separately decreases 0.86 g, 0.35 g and 0.26 g and that of the group 4 separately decreases 1.23 g, 0.50 g and 0.38 g. The results in FIG. 11 to FIG. 15 suggest that the HPMFs compound is able to inhibit the growth of the adipose tissue with a dose dependent manner.

Example 10

Biochemistry Assays of the Serum Collected from the Mice in the Each Group

After sacrificed the mice of the each group in example 7, the blood of the mice in the each group was collected. After centrifuge, the serum collected from blood of the each group was used for biochemistry assays to determine the concentrations of GOT, GPT, TG and T-cho in the serum. These measured biochemistry indexes are the typical indicators for liver functions shown in table 3.

TABLE 3

| Contents of the biochemistry function of liver in the each group | | | | |
|---|---|---|---|---|
| Group | GOT (U/L) | GPT (U/L) | TG (mg/dl) | T-cho (mg |
| 1 | 77.40 ± 9.15 | 19.00 ± 2.12 | 89.60 ± 28.61 | 80.60 ± 16.22 |
| 2 | 73.80 ± 29.02 | 29.80 ± 2.86# | 117.20 ± 20.87 | 140.20 ± 15.30 |
| 3 | 78.80 ± 15.78 | 27.20 ± 3.96 | 111.40 ± 13.31 | 130.40 ± 13.77 |
| 4 | 54.00 ± 13.69 | 25.60 ± 8.56 | 89.00 ± 21.42 | 119.00 ± 6.36 |

The results in table 3 show that the increased concentrations of GPT, TG and T-cho in the serum of mice in the group 2 with comparison of the group 1. Moreover, the concentrations of GOT, GPT, TG and G-cho in the serum of the mice in the group 3 and the group 4 are decreased with comparison of the group 2, respectively. Therefore, the results in table 3 suggest that the HPMFs compound has ability to lower the risk of fatty liver and lipid accumulation with a dose dependent manner.

Example 11

Histological Analysis of Liver in the Each Group

After sacrificed the mice of the each group in example 7, the liver collected from the sacrificed mice in each groups was fixed with formalin. After the fixation, the liver tissue of the each group was paraffin-embedded for histology section and analysis. The deparaffined histology sections of the four groups were subjected for hematoxyliene and eosin staining, respectively and shown in FIG. 16, wherein FIG. 16A to 16D sequentially present in the group 1 to 4.

According to FIG. 16, it shows that the hepatocytes of the mice in the group 2 reveal the histopathology resulted from accumulation of large amount of lipid-drops with comparison of the group 1. Comparing with the group 2, the group 3 can decrease the accumulation of oil-drops in hepatocytes. Furthermore, the group 4 not only decreases the accumulation lipid-drops in hepatocytes, but also prevents the abnormality occurred on the histology of hepatocytes. Therefore, it indicates the effect of the HPMFs compound for improving the hepatic histology with a dose dependent manner.

The present invention discloses the effects of the HPMFs compound for inhibiting adipocyte differentiation and maturation, and preventing fatty liver and lowering lipid accumulation. Therefore, the HPMFs compound plays an important role in a pharmaceutical composition for the purposes to suppress obesity and cure fatty liver. And based on the HPMFs compound extracted from the nature plants, it reveals no cellular toxicity and the lower side effects to a subject. Therefore, the HPMFs compound is capable of applying as the dietary composition for manufacture of the functional foods to improve the obesity and improving fatty liver.

The above-mentioned specification is only for detailed describing the examples of the invention and shall not be construed as a limitation of the scope of the invention Thus, any modification or change without departing from the characteristics of the invention or any equivalent thereof shall be included in the scope of the invention defined in the following claims.

What is claimed is:

1. A method of treating or preventing a disease selected from the group consisting of obesity, fatty liver, metabolic syndrome, insulin resistance syndrome, cardiovascular disease, hypertension and hyperlipidemia, comprising step A: taking a predetermined amount of an extract from a peel of citrus fruit;

step B: dissolving the extract with alcohols and then adding hydrochloric acid to obtain a first mixture;

step C: incubating the first mixture with heating circumfluence, and then removing the alcohols, so as to obtain a second mixture;

step D: extracting the second mixture by water and an organic solvent;

step E: collecting an organic phase obtained with the organic solvent, and then purifying, so as to obtain a hydroxyl polymethoxylflavones (HPMFs) compound; and step F: administering an effective amount of a composition to a subject, the composition including the hydroxyl polymethoxylflavones compound, a pharmaceutically acceptable salt thereof, or a mixture thereof.

2. The method of claim 1, wherein the citrus fruit is selected from the group consisting of pomelo, mandarin orange, orange, kumquat and lemon.

3. The method of claim 1, wherein the composition is a food composition.

4. The method of claim 1, wherein the composition is a pharmaceutical composition.

* * * * *